(12) United States Patent
Salgarelli

(10) Patent No.: US 6,936,063 B2
(45) Date of Patent: Aug. 30, 2005

(54) HIGHLY HEAT-CONDUCTIVE BODY WRAP

(75) Inventor: Silvio Salgarelli, Negrar (IT)

(73) Assignee: Technodesign SRL (IT)

( * ) Notice: Subject to any disclaimer, the term of this patent is extended or adjusted under 35 U.S.C. 154(b) by 136 days.

(21) Appl. No.: 10/472,556

(22) PCT Filed: Mar. 27, 2002

(86) PCT No.: PCT/IT02/00200
§ 371 (c)(1),
(2), (4) Date: Sep. 19, 2003

(87) PCT Pub. No.: WO02/078591
PCT Pub. Date: Oct. 10, 2002

(65) Prior Publication Data
US 2004/0116989 A1 Jun. 17, 2004

(30) Foreign Application Priority Data
Mar. 29, 2001 (IT) .................................. VR2001A0043

(51) Int. Cl.[7] .............................................. A61H 33/00
(52) U.S. Cl. ......................................... 607/85; 607/81
(58) Field of Search ........................... 607/81–87, 104; 604/290, 291; 4/568, 577.1

(56) References Cited

U.S. PATENT DOCUMENTS

| 2,930,594 | A | | 3/1960 | MacCraken |
| 3,961,380 | A | | 6/1976 | Garr |
| 5,411,494 | A | | 5/1995 | Rodriguez |
| 5,891,187 | A | | 4/1999 | Winthrop et al. |
| 6,406,447 | B1 | * | 6/2002 | Thrash et al. ............... 601/160 |
| 6,743,250 | B2 | * | 6/2004 | Renfro ....................... 607/104 |

FOREIGN PATENT DOCUMENTS

| DE | 195 31 856 | 3/1997 |
| EP | 0 098 390 A | 1/1984 |
| WO | WO 97 24088 | 7/1997 |
| WO | WO 99 44552 A | 9/1999 |

OTHER PUBLICATIONS

International Search Report of Oct. 29, 2002.

* cited by examiner

*Primary Examiner*—Roy D. Gibson
*Assistant Examiner*—Aaron Roane
(74) *Attorney, Agent, or Firm*—Greenberg Traurig, LLP; Neer Gupta, Esq.; Pablo E. Tapia, Esq.

(57) ABSTRACT

A highly heat-conductive body wrap (10) comprises a casing (13) made of highly flexible, elastic material and equipped with means for fastening it to the shell (11) of a tub (12) for cosmetic treatments. The casing (13) has at least one base portion (14) and side compartments (15, 16), at least one (16) of the side compartments (15, 16) being connected to a water system designed to distribute hot liquid within it.

9 Claims, 2 Drawing Sheets

HIGHLY HEAT-CONDUCTIVE BODY WRAP

This application is the national stage under 35 U.S.C. § 371 of PCT International Application No. PCT/IT02/00200, filed on Mar. 27, 2002, which in turn claims priority to Italian Application No. VR2001A000043 filed Mar. 29, 2001. The contents of all these applications are herein incorporated by reference in their entirety.

TECHNICAL FIELD

The present invention relates to a highly heat-conductive body wrap used in cosmetic and/or medical treatments for body care.

In particular, the present invention relates to a body wrap made, advantageously, of highly flexible and elastic plastic and whose structure is such that it can be used in conjunction with a tub for physical wellness and beauty treatments.

BACKGROUND ART

The use of hot tubs for cosmetic and beauty treatments is well known.

These tubs comprise a shell designed to contain a liquid that can be heated by suitable thermostatically controlled means and transferred using pumps or other suitable machinery.

The opening of the tub shell is covered entirely by an impermeable body wrap in direct contact with the heated liquid in such a way as to transmit heat to the wrap not only by conduction but also by convective motion.

The wrap is made of an elastic and flexible plastic material. When a user lies back in the tub, the wrap adapts to his/her shape and folds over to completely wrap up his/her body.

Usually, the user's skin is covered with cosmetic products which are softened and melted by the heat transmitted by the wrap, giving a sense of wellness and guaranteeing uniformity of treatment thanks to the adhesion of the wrap to the body.

The tub is usually connected to an external water supply so that the heating liquid can be continuously recycled in such a way as to favour convective motion in the areas in contact with the wrap.

This type of tub is particularly suitable for skin care treatments, including mud therapy, and can be used for a wide variety of applications in the cosmetics sector.

EP-A-0098390 describes for example a body wrap made of an elastic and flexible material which covers entirely the opening of a tub shell and is in direct contact with the heated liquid in such a way to transmit the heat to the wrap.

When a user lies back in the tub, the wrap adapts to his/her shape and folds over to completely wrap up his/her body. The tub is usually connected to an external water supply so that the heating liquid can be continuously recycled in such a way as to favour convective motion in the areas in contact with the wrap.

One disadvantage, however, is the fact that the wrap adheres perfectly to the lower part of the user's body, which is on the same side as the tub shell, but does not adhere uniformly to the upper side of the body, which faces the outside of the shell.

Another disadvantage is the fact that the convective motion of the hot liquid is effective at the portion of the wrap that is in contact with the lower part of the user's body, but does not efficiently reach the parts of the wrap which are folded over the upper part of the user's body.

Thus, to ensure uniform treatment, the user is obliged to lie first on his/her back for one part of the treatment and then turn round to lie on his/her stomach to complete the treatment.

Moreover, the weak convective motion of the liquid at the upper folds of the wrap, significantly reduces the wellness effect because of the different temperature gradient felt by the user between the upper and lower portions of the wrap.

With reference to the medical field, several systems to regulate the body temperature in abnormal condition are known.

WO-A-9944552 describes a system and a method for controlling an individual's body and temperature. Said system comprises a heat exchanger for transferring heat to or removing heat from portions of the individual's body surface with the aim to allow controlled cooling of the body temperature, controlled heating, as well as regulating an individual's body temperature to remain at a desired set temperature. It is a unique feature of the system according to WO-A-9944552 that it takes into consideration the complexity of the heat transfer regiment from the skin to the body's core. In order to be effective in cooling or heating, the heat exchanger according to WO-A-9944552 has typically the form of a garment and has to be fitted onto the individual's skin.

This is very different from the aim of the present invention which provides a highly heat-conductive body wrap to be used connected to hot tubs for cosmetics and beauty treatments were the user's skin is covered with cosmetics products or with mud in the case for example of mud baths.

U.S. Pat. No. 5,411,494 describes an apparatus for warming, delivering, and distributing the water flow over at least fifty percent of the body surface of a subject and for collecting spent water into a receptacle. Said apparatus comprises a system of water-permeable water distribution tubes supplied with temperature-controlled water which distributes water over an area of an adsorbent web.

In the case of U.S. Pat. No. 5,411,494 the system is developed to be used in the medical field to regulate the body temperature particularly in the case hyperthermia.

DESCRIPTION OF THE INVENTION

The present invention has for an aim to provide a highly heat-conductive body wrap capable of overcoming or significantly reducing the above mentioned disadvantages.

Another aim of the present invention is to provide a highly heat-conductive body wrap that is easy to apply to any type of tub for physical wellness and beauty treatments.

These aims are accomplished by a highly heat-conductive body wrap for cosmetic and/or medical treatments having the features described in the main claim.

The dependent claims describe advantageous embodiments of the invention.

The highly heat-conductive body wrap sheet according to the invention comprises a two-ply casing made of highly flexible, elastic material, equipped with means for fastening it to the shell of a tub for physical wellness and beauty treatments, said casing having at least one base portion and side compartments, at least one of which is connected to a water system and designed to hold continuously recycled liquid.

According to the invention, the side compartment has a device for distributing the liquid inside it.

The distribution device may consist of a main flexible tube to which there may be connected two or more secondary branch tubes uniformly distributed within the compartment itself and equipped with outflow holes.

In one embodiment, the distribution device consists of a plurality of longitudinal, intercommunicating chambers having respective openings leading into the side compartment.

Advantageously, the water system used to supply the tub shell is the same as the one used to supply the hot liquid to the side compartment.

The water system includes an electric pump which, for safety, operates on low-voltage power.

When the user lies in the tub, the base portion of the body wrap guarantees good adhesion to his/her skin, favouring the exchange of heat with the hot liquid in the tub shell, while the upper portion with the side compartments, allows good heat transfer thanks to the liquid from the distribution device.

DESCRIPTION OF THE DRAWINGS

The characteristics and advantages of the invention are apparent from the detailed description which follows, with reference to the accompanying drawings which illustrate a preferred embodiment of the invention provided merely by way of example without restricting the scope of the inventive concept, and in which.

DESCRIPTION OF A PREFERRED EMBODIMENT

Figure 3:
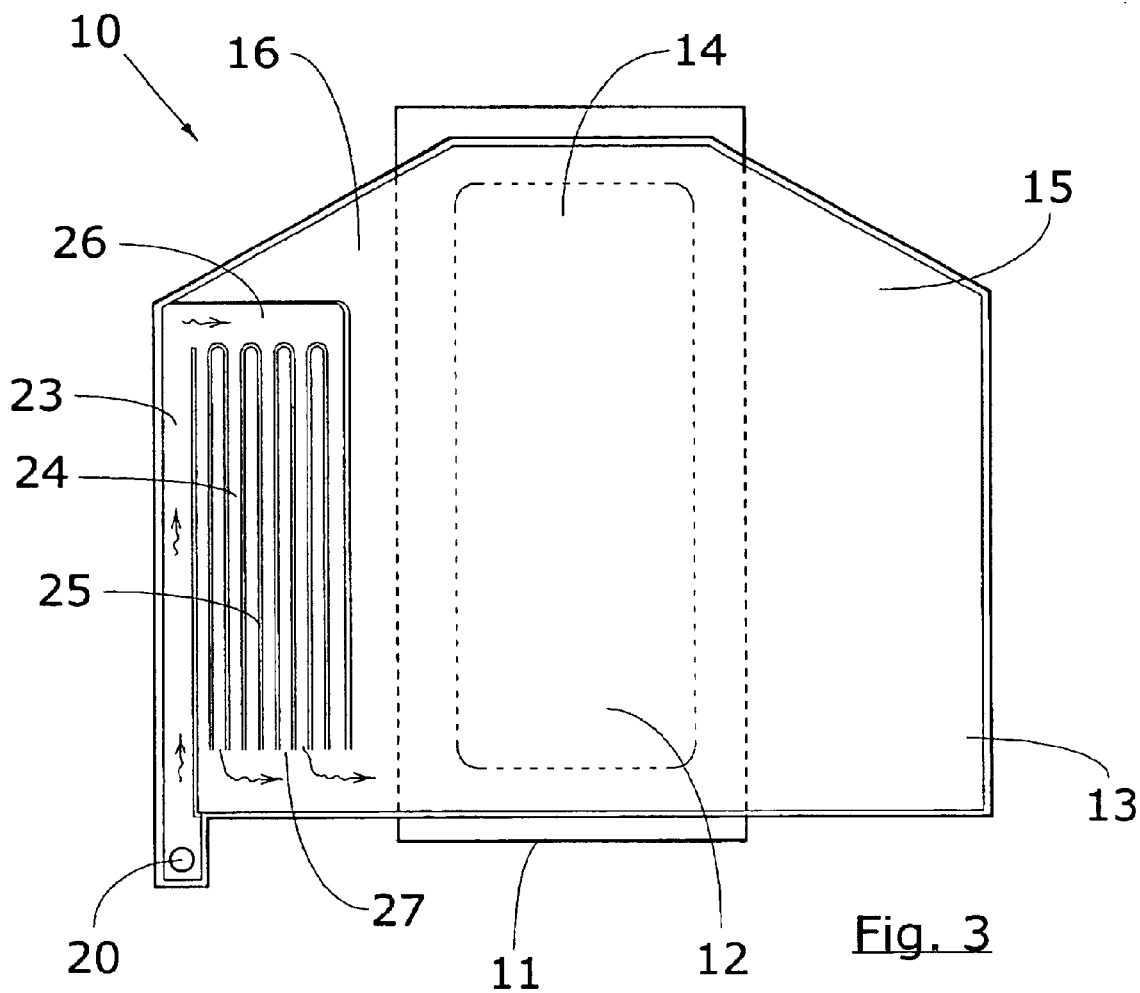
FIG. 3 is a plan view, with some parts in cross section, of another embodiment of the body wrap according to the invention.
Figure 1:
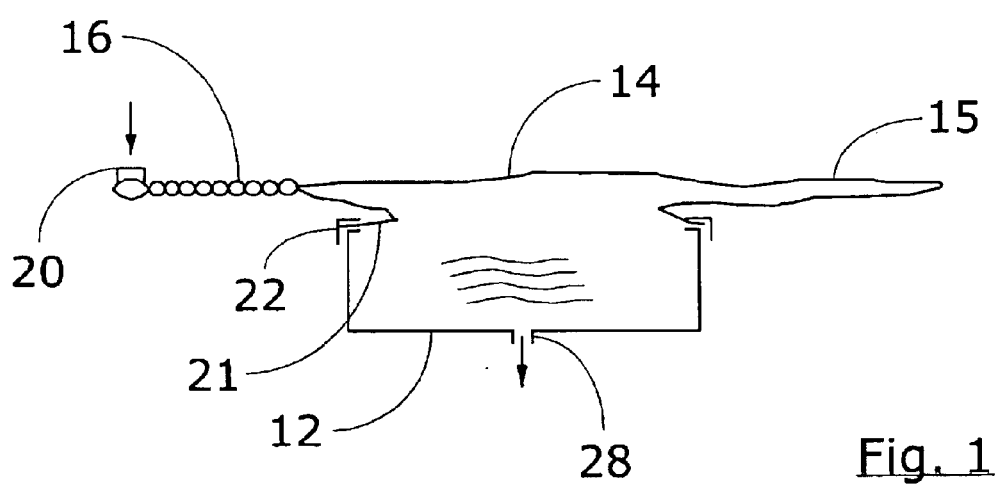
FIG. 1 is a front view of the body wrap according to the invention in working conditions.

With reference to the accompanying drawings, the numeral 10 denotes in its entirety a highly heat-conductive body wrap, in particular a wrap 10 fastened to the shell 11 of a tub 12 for physical wellness and beauty treatments.

The wrap 10 consists of a casing 13 made of a highly flexible and elastic material and having at least one base portion 14 and side compartments 15 and 16.

Figure 2:
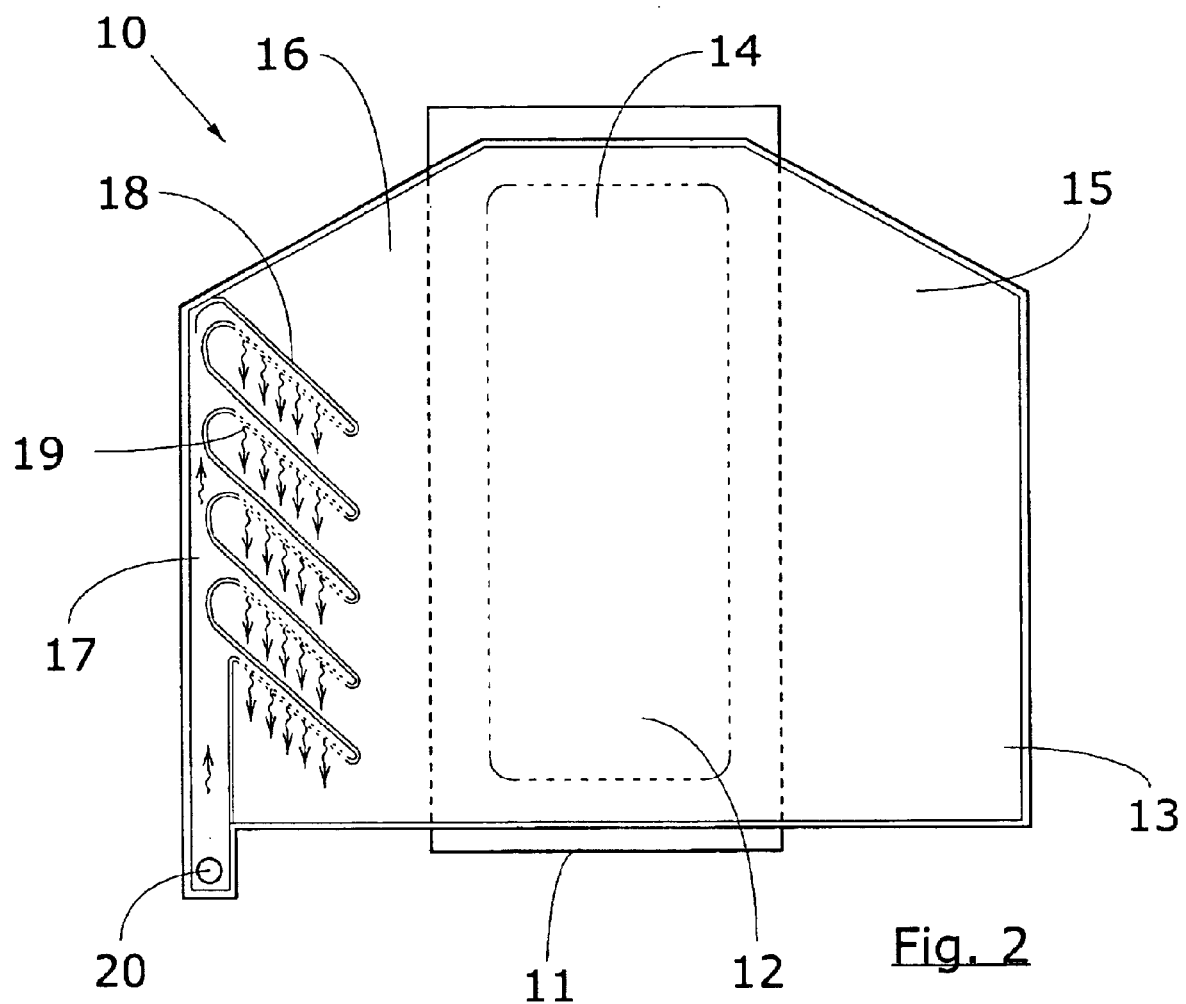
FIG. 2 is a plan view of a body wrap with some parts in cross section.

As shown in FIG. 2, the interior of the compartment 16 presents a main tube 17 to which there can be connected to two or more secondary branch tubes 18 uniformly distributed inside the compartment 16 itself and having outflow holes 19.

The secondary tubes 18 extend transversally along the back of the compartment 16 preferably parallel to each other and inclined to the main tube not necessarily at right angles.

The holes 19 may be aligned on a respective secondary tube 18 facing the main tube 17.

The latter protrudes partly from the compartment 16 and has, at the free end of it, a fitting 20 for connecting it to a water system (not illustrated in the drawings) designed to supply a continuously recycled hot liquid.

The perimetric edge 21 of the wrap 10 is designed to be retained inside a respective fastener 22 which is integral with the upper edge of the shell 11 in such a way as to form effective means for attaching the wrap 10 to the tub 12.

The hot liquid flows uniformly through the interior of the whole compartment 16, first through the main tube 17 in the direction indicated by the arrow and then enters each of the secondary tubes 18 and flows out through the holes 19.

In the embodiment illustrated in FIG. 3, the side compartment 16 is equipped with a device for distributing hot liquid consisting of a plurality of intercommunicating longitudinal chambers 23 and 24.

Each chamber 23 and 24 is separated from the adjacent chamber by ribs 25, consisting, for example, of sealed seams extending lengthways along most of the compartment 16 and leaving room for a connecting zone 26, at the far end relative to the fitting 20, and for a set of outflow openings 27 on the side opposite the zone 26.

In this embodiment, the hot liquid flows into the main tube through the fitting 20 and, from the main tube, into each chamber 24 and out through the holes 27.

The liquid flowing out of the holes 27 is then recycled into the tub 12.

The side compartments 15 and 16 may be in direct communication with the inside of the tub 12 so as to use the same hot liquid as that in the shell 11, the liquid being transferred from one point in the system to another by any conventional machine (not illustrated).

The machine may consist of an electric pump which, for safety, operates on low-voltage power.

The bottom of the shell 11 normally has at least one opening 28 designed to allow the hot liquid to flow out. The hot liquid flows back in through the fitting 20 and falls into the tub 12 after flowing through the side compartment 16, thus being continuously recycled.

When a user lies in the tub 12, the base portion 14 of the body wrap 10 is deformed in such a way as to wrap the user's body and to adhere to his/her skin. Under these conditions, heat can be effectively transferred by the hot liquid in the shell 11.

The side compartments 16 and 15 are folded over the top of the user to the closed position. In particular, the compartment 16 is positioned in direct contact with the user's skin so as to allow the heat of the hot liquid to be effectively transferred.

The invention has been described with reference to a preferred embodiment of it.

Therefore, it will be understood that the invention may be modified and adapted in several ways without thereby departing from the scope of the inventive concept.

What is claimed is:

1. A tub for cosmetic and beauty treatments comprising:
 a highly heat-conductive body wrap having a casing made of highly flexible, elastic material and equipped with fixing means, wherein the casing has at least one base portion, and side compartments and which are foldable over the base portion to cover a body laying on the wrap, whereby said wrap is a two-ply sheet, at least one of the side compartments being connectable to a water system and comprising an open device for distributing hot liquid over the internal surface of said at least one compartment when it is folded over said body; and
 a water system for the supply of hot liquid to a shell of the tub or to the side compartment of the wrap.

2. A tub according to claim 1 characterized in that the hot liquid flowing in the open device is collected inside the tub.

3. A tub for cosmetic and beauty treatments comprising:
 a highly heat-conductive body wrap having a casing made of highly flexible, elastic material and equipped with fixing means, wherein the casing has at least one base portion, and side compartments and which are foldable over the base portion to cover a body laying on the wrap, whereby said wrap is a two-ply sheet, at least one of the side compartments being connectable to a water system and comprising an open device for distributing hot liquid over the internal surface of the said at least one compartment when it is folded over said body;

a water system for the supply of hot liquid to a shell of the tub or to the side compartment of the wrap; and wherein the distribution device consists of a main tube, connectable to the water system, and communicating with a plurality of secondary branch tubes uniformly distributed within the side compartment and having a plurality of outflow holes.

4. A wrap according to claim 3, characterised in that the distribution device consists of a plurality of intercommunicating longitudinal chambers.

5. A tub for cosmetic and beauty treatments comprising:

a highly heat-conductive body wrap having a casing made of highly flexible, elastic material and equipped with fixing means, wherein the casing has at least one base portion, and side compartments and which are foldable over the base portion to cover a body laying on the wrap, whereby said wrap is a two-ply sheet, at least one of the side compartments being connectable to a water system and comprising an open device for distributing hot liquid over the internal surface of the said at least one compartment when it is folded over said body;

a water system for the supply of hot liquid to a shell of the tub or to the side compartment of the wrap;

wherein the distribution device consists of a main tube, connectable to the water system, and communicating with a plurality of secondary branch tubes uniformly distributed within the side compartment and having a plurality of outflow holes; and wherein the holes are aligned on each of the secondary tubes.

6. A tub for cosmetic and beauty treatments comprising:

a highly heat-conductive body wrap having a casing made of highly flexible, elastic material and equipped with fixing means, wherein the casing has at least one base portion, and side compartments and which are foldable over the base portion to cover a body laying on the wrap, whereby said wrap is a two-ply sheet at least one of the side compartments being connectable to a water system and comprising an open device for distributing hot liquid over the internal surface of the said at least one compartment when it is folded over said body;

a water system for the supply of hot liquid to a shell of the tub or to the side compartment of the wrap; and wherein the distribution device consists of a plurality of interconnecting longitudinal chambers.

7. A tub for cosmetic and beauty treatments comprising:

a highly heat-conductive body wrap having a casing made of highly flexible, elastic material and equipped with fixing means, wherein the casing has at least one base portion, and side compartments and which are foldable over the base portion to cover a body laving on the wrap, whereby said wrap is a two-ply sheet, at least one of the side compartments being connectable to a water system and comprising an open device for distributing hot liquid over the internal surface of the said at least one compartment when it is folded over said body; and a water system for the supply of hot liquid to a shell of the tub or to the side compartment of the wrap;

wherein the distribution device consists of a plurality of intercommunicating longitudinal chambers; and wherein each chamber is separated from the adjacent chamber by ribs extending lengthways along most of the compartment.

8. A wrap according to claim 7 characterised in that each longitudinal chamber has an outflow opening leading into the compartment.

9. A tub for cosmetic and beauty treatment comprising:

a highly heat-conductive body wrap having a casing made of flexible, elastic material and equipped with fixing means, wherein the casing has at least one base portion, and side compartments and which are foldable over the base portion to cover body laying on the wrap, whereby said wrap is a two-ply sheet, at least one of the side compartments being connectable to a water system and comprising an open device for distributing hot liquid over the internal surface of the said at least one compartment when it is folded over said body;

a water system for the supply of hot liquid to a shell of the tub or to the side compartment of the wrap;

wherein the distribution device consists of a plurality of intercommunicating longitudinal chambers; and wherein each longitudinal chamber has an outflow opening leading into the compartment.

\* \* \* \* \*